(12) United States Patent
Seidenberger

(10) Patent No.: US 10,857,332 B2
(45) Date of Patent: Dec. 8, 2020

(54) INSERTION CATHETER HAVING A VALVE BODY

(71) Applicant: JOLINE GMBH & CO. KG, Hechingen (DE)

(72) Inventor: Dieter Seidenberger, Hechingen (DE)

(73) Assignee: JOLINE GMBH & CO. KG, Hechingen (DE)

( * ) Notice: Subject to any disclaimer, the term of this patent is extended or adjusted under 35 U.S.C. 154(b) by 190 days.

(21) Appl. No.: 16/091,407

(22) PCT Filed: Mar. 31, 2017

(86) PCT No.: PCT/EP2017/057771
§ 371 (c)(1),
(2) Date: Oct. 4, 2018

(87) PCT Pub. No.: WO2017/178256
PCT Pub. Date: Oct. 19, 2017

(65) Prior Publication Data
US 2019/0151622 A1 May 23, 2019

(30) Foreign Application Priority Data

Apr. 11, 2016 (DE) .................. 10 2016 106 626

(51) Int. Cl.
*A61M 25/06* (2006.01)
*A61M 39/06* (2006.01)
(Continued)

(52) U.S. Cl.
CPC ........ *A61M 25/0662* (2013.01); *A61M 29/02* (2013.01); *A61M 39/06* (2013.01);
(Continued)

(58) Field of Classification Search
CPC .............. A61M 25/0662; A61M 39/06; A61M 39/0606; A61M 2039/0633; A61M 2039/064
See application file for complete search history.

(56) References Cited

U.S. PATENT DOCUMENTS 5,360,417 A * 11/1994 Gravener ........... A61B 17/3462
251/5
5,827,227 A 10/1998 DeLago
(Continued)

FOREIGN PATENT DOCUMENTS

| CA | 2235609 C | 3/2007 |
|---|---|---|
| EP | 0442194 A2 | 8/1991 |

(Continued)

OTHER PUBLICATIONS

International Search Report and Written Opinion Form PCT/ISA/210 and PCT/ISA/237, International Application No. PCT/EP2017/057771, pp. 1-8, International Filing Date Mar. 31, 2017, dated Jul. 13, 2017.
(Continued)

*Primary Examiner* — Bradley J Osinski
(74) *Attorney, Agent, or Firm* — Bond Schoeneck & King, PLLC; George McGuire

(57) ABSTRACT

A delivery catheter including a valve body having a closeable valve opening for introducing a medical device in insertion direction into, in particular, a blood vessel, the valve opening, when a medical device is not introduced, tapering in the insertion direction, and a sealing section, which in a closed position at least in sections is subject to a pretension, directly adjoins the taper, so that the sealing section, when a medical device is introduced, is actuated from the closed position into an open position in such manner that the sealing section encloses the medical device in a substantially fluid-tight manner.

12 Claims, 8 Drawing Sheets

(51) Int. Cl.
 *G06F 21/57* (2013.01)
 *A61M 29/02* (2006.01)
(52) U.S. Cl.
 CPC ....... *A61M 39/0606* (2013.01); *G06F 21/572* (2013.01); *A61M 2039/062* (2013.01); *A61M 2039/064* (2013.01); *A61M 2039/0633* (2013.01)

(56) References Cited

U.S. PATENT DOCUMENTS

| | | | |
|---|---|---|---|
| 2004/0267202 A1* | 12/2004 | Potter | A61M 39/06 604/158 |
| 2007/0106262 A1* | 5/2007 | Becker | A61M 39/0606 604/533 |
| 2010/0100044 A1 | 4/2010 | Ye et al. | |
| 2010/0312190 A1 | 12/2010 | Searfoss et al. | |

FOREIGN PATENT DOCUMENTS

| | | |
|---|---|---|
| EP | 2039389 B1 | 6/2011 |
| EP | 3000503 A1 | 3/2016 |
| EP | 2762193 B1 | 10/2016 |
| JP | 2007523680 A | 8/2007 |
| JP | 2009512509 A | 3/2009 |
| WO | 2009002828 A2 | 12/2008 |

OTHER PUBLICATIONS

Translated Reasons for Rejection.

\* cited by examiner

INSERTION CATHETER HAVING A VALVE BODY

CROSS-REFERENCE TO RELATED APPLICATIONS

This application is the United States National Phase Application of PCT Application No. PCT/EP2017/057771 filed on Mar. 31, 2017, which claims priority to German Application No. DE 102016106626.5 filed on Apr. 11, 2016, the entire disclosure of each of which is incorporated herein by reference.

BACKGROUND

The present invention relates to a delivery catheter including a valve body having a closeable valve opening for introducing a medical device in the insertion direction, in particular, a blood vessel. Moreover, the present invention relates to an associated valve and a delivery catheter-dilator assembly.

The introduction of medical devices, for example catheters, into blood vessels has been known for many years for a plurality of applications. For example, stents are released into blood vessels or implanted into long-term implants with the aid of introduced catheters. Furthermore, dialysis catheters are implanted. On the other hand, the catheters are also used for introducing or removing fluids from various vascular regions in the body. The introduction of catheters into the body is particularly delicate and complex. One difficulty for the so-called catheterization is the enlargement of the puncture hole in the blood vessel to be catheterized and, in this instance, to simultaneously keep the blood loss and the burden for the patient as low as possible. A method frequently used for this purpose is the so-called Seldinger method. This method involves the surgical opening of a vein or artery by a needle, the introduction of a guide wire through the lumen of the needle into the vein or artery, the retraction of the needle, the introduction of a delivery catheter-dilator assembly along the guide wire, the removal of the dilator and the introduction of the actual catheter through the delivery catheter into the blood vessel. After introducing the catheter, the delivery catheter is regularly removed in that it is pulled apart in a zipper-like manner and removed.

To keep blood loss during this complex procedure to a minimum, delivery catheters usually have a hemostasis valve having a closeable valve opening regularly formed in a slit-shaped manner.

From CA 02235609 C, a delivery catheter is known. The valve opening there disclosed mostly has a taper and an extension connecting thereto. In this instance, the extension is cylindrically formed and has a base which runs transverse to the direction of insertion. This base has a slit.

Another delivery catheter is known from EP 2 039 389 B1.

Furthermore, various types of such valves are known from the prior art. Regularly, each valve is configured for use with a particular catheter size. For this reason, it is not possible to use one single valve with catheters of very different diameters and outer contours. In particular, the valve openings regularly are adapted to the object to be introduced and, for example, have a round or oval cross section of a certain size. In this instance, the valves are regularly cylindrically formed having parallel top and bottom sides, the valve opening being formed as a curve or slit extending from the top to the bottom. If then medical devices are introduced through the valve opening to which they are not adapted, the valves wave, in particular their top and bottom sides, and no longer reliably seal the valve opening.

Accordingly, it is the object of the present invention to provide a delivery catheter which can be used more flexibly.

SUMMARY OF THE INVENTION

This object is achieved by a delivery catheter.

In the following, it is provided that, when a medical device is not introduced, the valve opening tapers in the insertion direction and a sealing section directly adjoins the tapering.

If no medical device is introduced, the sealing section and, for this reason, the valve thus take on a fluid-tight closed position, in which the sealing section at least in sections is subject to pretension. If a medical device is introduced through the valve body, the sealing section is actuated from a closed position into an open position, in which the sealing section encloses the medical device substantially in a fluid-tight manner. Fluid-tight substantially means that no fluid escapes from the blood vessel or at least no fluid stream flows out of the blood vessel.

Owning to the taper, a medical device can be introduced into a blood vessel with relatively little friction. The reduced friction also reduces the propensity for undesirable creasing of the valve body. This results in that the valve body encloses an introduced medical device in a fluid-tight manner. The pretension onto the sealing section acts, when a medical device is introduced, also against this medical device. Overall, the combination of taper and pretension can ensure a fluid-tight enclosure of medical devices introduced into a blood vessel through the valve body.

On the one hand, the pretension for this purpose can also be exerted via an attachment section, at which the valve body is attached to the catheter, onto the valve body—and when a medical device is introduced, also onto this medical device. On the other hand, it is also conceivable that the valve body is formed in such a manner that it can exert an intrinsic pretension onto the sealing section so that a fluid-tight closing position is ensured if no medical device is introduced in the blood vessel. For this purpose, the pretension can be applied along the entire circumference of the sealing section or only along a portion of the circumference.

For this purpose, the valve opening in the area of the sealing section can be configured, in particular, in a slit-like manner. The extension of the slit in this instance can approach the value 0 so that the valve opening in the area of the sealing section can be formed as a substantially punctiform penetration.

Overall, providing a taper in the valve opening and the pretension onto the sealing section, medical devices, in particular catheters, of different geometries and dimensions can be introduced through the valve body into the blood vessels. Still, even if a medical device is introduced, it can be ensured that blood loss from a blood vessel is completely or substantially completely prevented.

Preferably, the sealing section in the insertion direction is located in the center region, in particular at the center, of the valve opening. In so doing, a particularly advantageous sealing can be provided.

In this instance, it has been proven to be particularly advantageous if the valve opening has an extension adjoining the sealing section in the insertion direction and expanding when no medical device is introduced. In this instance, the extension can have the same geometry as the taper. It has been shown that, in so doing, a particularly flexibly usable valve opening can be provided, which is fluid-tight also when different medical devices are introduced.

In this instance, the taper can be mirror-symmetrical in relation to a mirror plane extending through the valve opening along the insertion direction. The same applies to the extension. If the valve opening in the region of the sealing section is formed in a slit-like manner, the mirror plane can extend along the slit. In so doing, in particular also in an advantageous manner, a uniform pretension for sealing the slit can be applied onto the sealing section.

It has been proven to be particularly advantageous if the valve opening is mirror-symmetrical to a mirror plane extending transverse to the insertion direction through the sealing section. As a consequence, the taper and the extension can be mirror-symmetrical to each other. In so doing, a sealing can be provided in a particularly advantageous manner.

In this instance, the valve opening in the insertion direction can taper toward the sealing section in an arcuate, wave-like or linear manner. In addition, or alternatively, the valve opening starting from the sealing section can extend in the insertion direction in an arcuate, wave-like or linear manner. In this instance, the arcuate taper and/or extension can be configured in a convex or concave manner. Correspondingly, an arcuate taper and/or extension can include convex and concave sections.

It has been proven to be particularly advantageous if the valve body section surrounding the valve opening is configured in an elliptical manner and the valve opening extends in a slit-shaped manner in the region of the sealing section transverse to the insertion direction along the major axis of the elliptical valve body section. In this instance, it is conceivable that the pretension onto the sealing section is applied only transverse in relation to the major axis. On the other hand, it is also conceivable that the pretension acts upon the entire circumference of the sealing section.

Furthermore, it is conceivable that the taper and/or the extension has/have two first sections, which are mirror-symmetrical to a mirror plane extending in the insertion direction through the valve opening, and that the taper has two second sections extending semi-conically toward the corners of the slit-shaped valve opening. This geometry has been proven to be particularly advantageous with regard to the sealing when a medical device is introduced and with regard to friction during insertion of the medical device.

Advantageously, the valve body has a flange section for situating the valve at a catheter. For this purpose, the valve body can be mounted on the catheter, and the flange section for configuring a plug connection can have at least one mandrel or one recess, and the catheter can have at least one corresponding recess or one mandrel. On the other hand, it is also conceivable that the delivery catheter is formed as a single piece with the valve body.

For this purpose, the valve body can be made from silicone, in particular 8-25 Shore A, or it can include this material. This polymer material has proven to be particularly advantageous with regard to elasticity, abrasion and friction when introducing a medical device.

To reduce friction when introducing a medical device through the valve opening, a coating can be provided at least in the region of the sealing section. This coating can be made from silicone oil or include silicone oil. On the other hand, coatings which do not contain silicone oil are also conceivable.

Preferably, the outside of the valve body has at least one valve groove to form a predetermined breaking point. Moreover, the outside of the valve body can have at least one catheter groove situated in the same plane as the valve groove to form a predetermined breaking point, the catheter groove together with the catheter being produced by way of extrusion or injection molding. Consequently, the catheter groove does not have to be introduced separately in a further production step. This enables the removal of the delivery catheter in a simple manner after a medical device has been introduced into a blood vessel.

The object is also achieved by a valve body for a catheter according to the present invention. Therefore, the valve body includes a closeable valve opening, the valve opening tapering in the direction of insertion when a medical device is not introduced, and a sealing section adjoining the taper. In so doing, provided is a valve which can be used in a particularly flexible manner and through which medical devices of different geometries and cross sections can be introduced, and a fluid-tight sealing can still be provided.

Finally, the object of the present invention is also achieved by a delivery catheter-dilator assembly including a catheter according to the present invention and a dilator situated at the catheter, the dilator extending in sections through the catheter. This assembly is in particular suitable for use in catheterization by way of the so-called Seldinger method.

Further details and advantageous embodiments of the present invention can be concluded from the subsequent description, on the basis of which exemplary embodiments of the present invention are described and explained in greater detail.

BRIEF DESCRIPTION OF THE DRAWINGS

In the figures.

DETAILED DESCRIPTION

Figure 1:
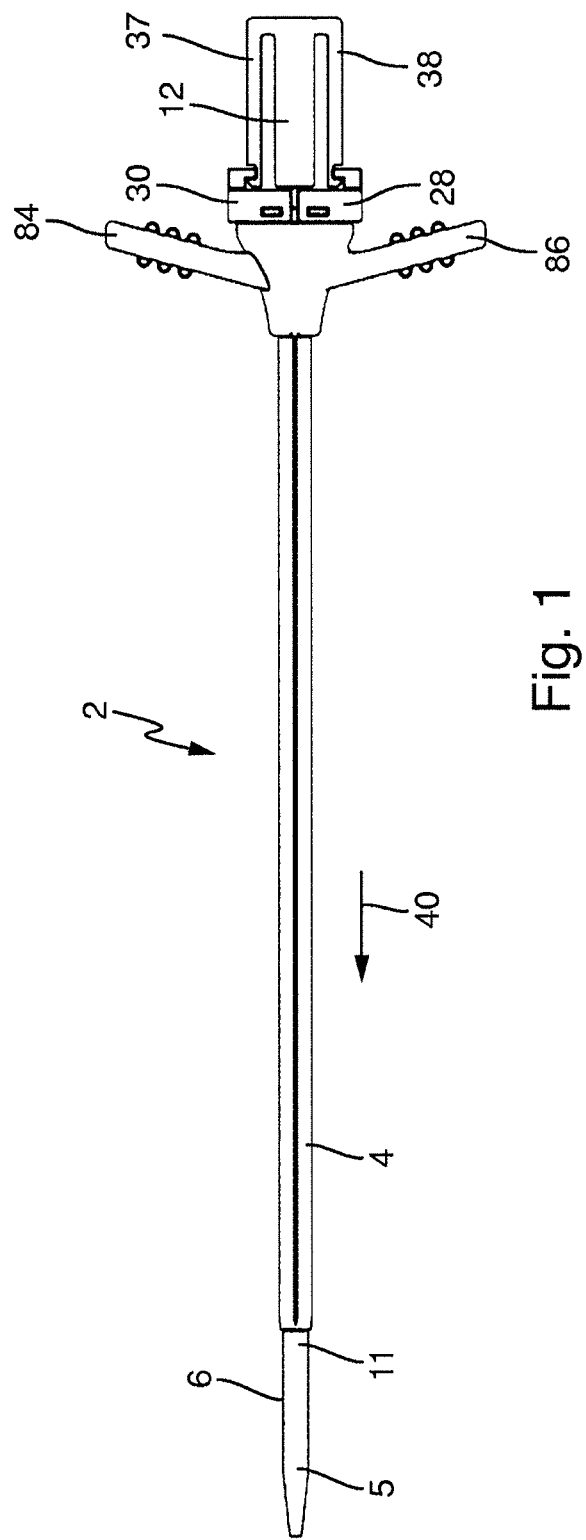
FIG. 1 shows a schematic side view of a delivery catheter-dilator assembly.
Figure 2:
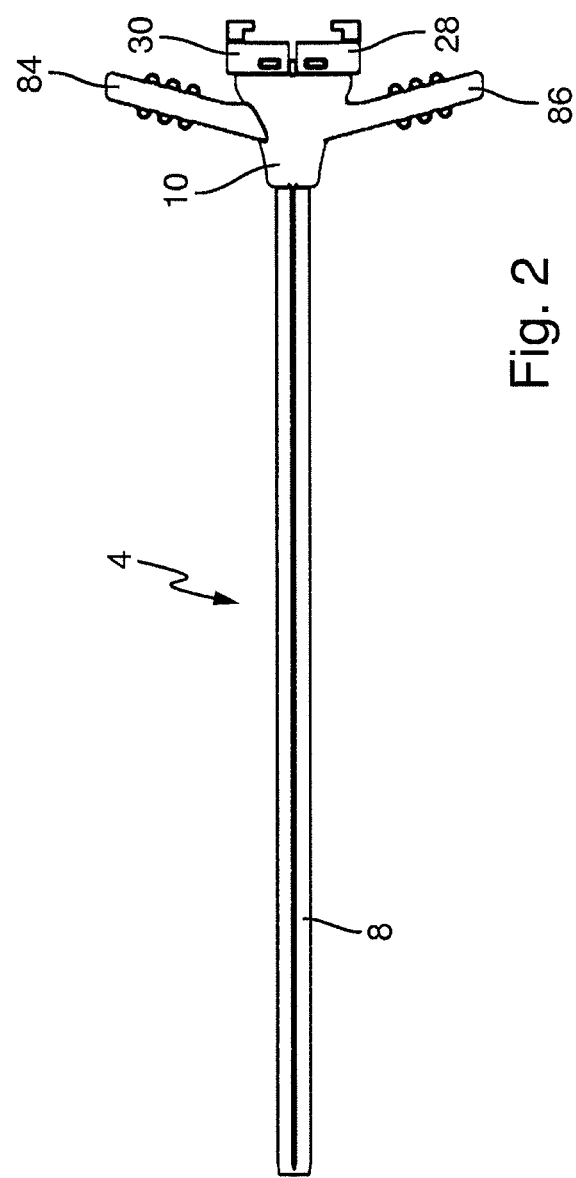
FIG. 2 shows a schematic side view of the catheter of the assembly according to FIG. 1.
Figure 3:
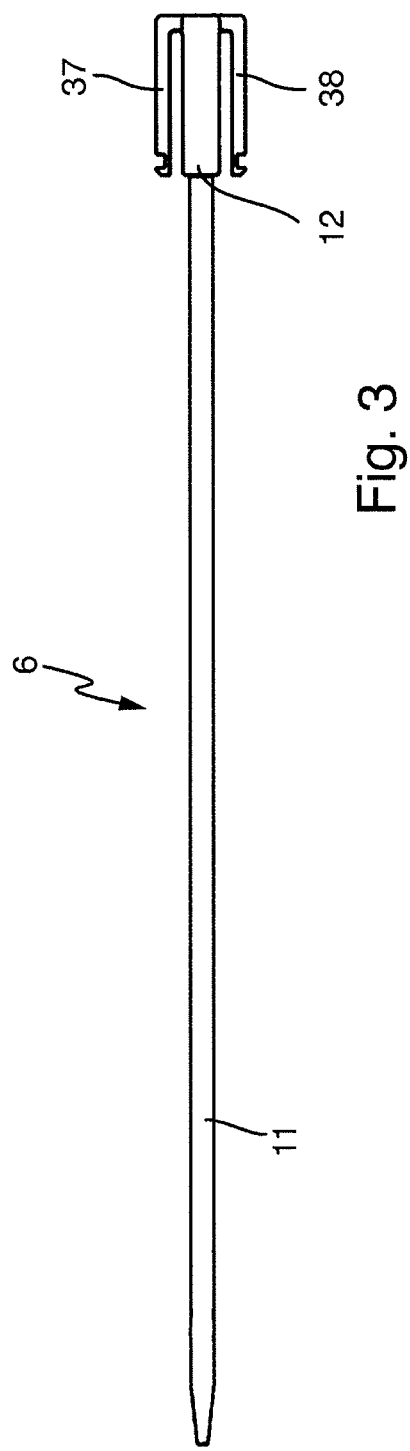
FIG. 3 shows a schematic side view of the dilator of the assembly according to FIG. 1.

FIG. 1 shows a delivery catheter dilator assembly denoted in total with reference character 2, including a delivery catheter 4 and a dilator 6 situated thereon. In this instance, delivery catheter 4 has a tube section 8 and a head section 10 (cf. FIG. 2). Dilator 6 also has a tube section 11 and a head section 12 (cf. FIG. 3). Tube section 11 of the dilator extends in this instance through tube section 8 of delivery catheter 4, tip 5 of dilator 6 projecting out of the delivery catheter.

Figure 4:
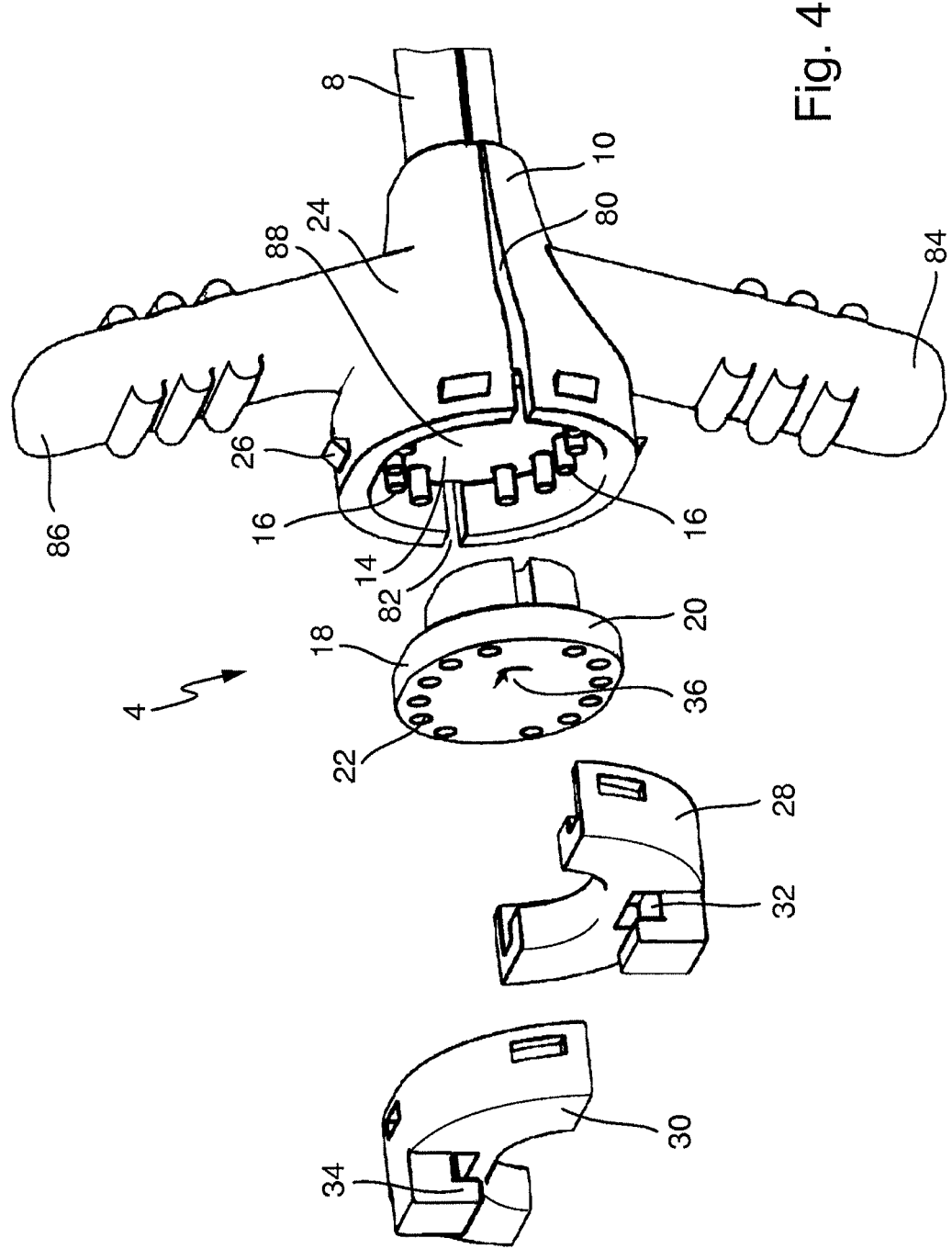
FIG. 4 shows an exploded view of the delivery catheter according to FIG. 2.

As can be clearly seen from FIG. 4, head section 10 of delivery catheter 4 has an attachment section 14. Attachment section 14 includes a plurality of mandrels 16. A valve body 18 is situated at this attachment section 14. For this purpose, valve body 18 has a flange section 20 having a plurality of recesses 22, which correspond with mandrels 16 so that valve body 18 is pluggable by way of a plug connection onto attachment section 14.

Furthermore, outside 24 of attachment section 10 has a plurality of protrusions 26. Two holding parts 28, 30 are clippable to these protrusions. In turn, holding parts 28, 30 each have one locking means 32, 34, into which locking hooks 37, 38 provided at attachment section 12 of dilator 6 can latch, as it can be seen in FIG. 1.

As can be concluded from FIGS. 5 to 9, valve body 18 has a closeable valve opening 36, which extends from a top side 37 to a bottom side 39 of valve body 18. In this instance, valve opening 36 tapers in insertion direction 40. A sealing section 44 directly adjoins this taper 42 in insertion direction 40. For this purpose, sealing section 44 is located in the center region of valve opening 36. In turn, an extension 46 directly adjoins sealing section 44 in insertion direction 40.

In this instance, valve opening 36 expands into extension 46 in insertion direction 40 to the same extent as valve opening 36 tapers into taper 42. Consequently, valve opening 36 is mirror-symmetrical in relation to a mirror plane 48 extending transverse to insertion direction 40 through sealing section 44.

Moreover, valve opening 36 or entire valve body 18 is mirror-symmetrical in relation to a mirror plane 52 extending along insertion direction 40 through valve opening 36. In this instance, mirror plane 52 extends moreover along slit-shaped valve opening section 54 limited by sealing section 44, as it is shown in FIG. 9.

Valve body section 50 adjoining flange section 20 in insertion direction 40 (cf. FIGS. 8 and 9) is elliptically formed. For this purpose, slit-shaped valve opening section 54 in the region of sealing section 44 extends transverse to insertion direction 40 along the major axis of this elliptical valve body section 50.

Figure 9:
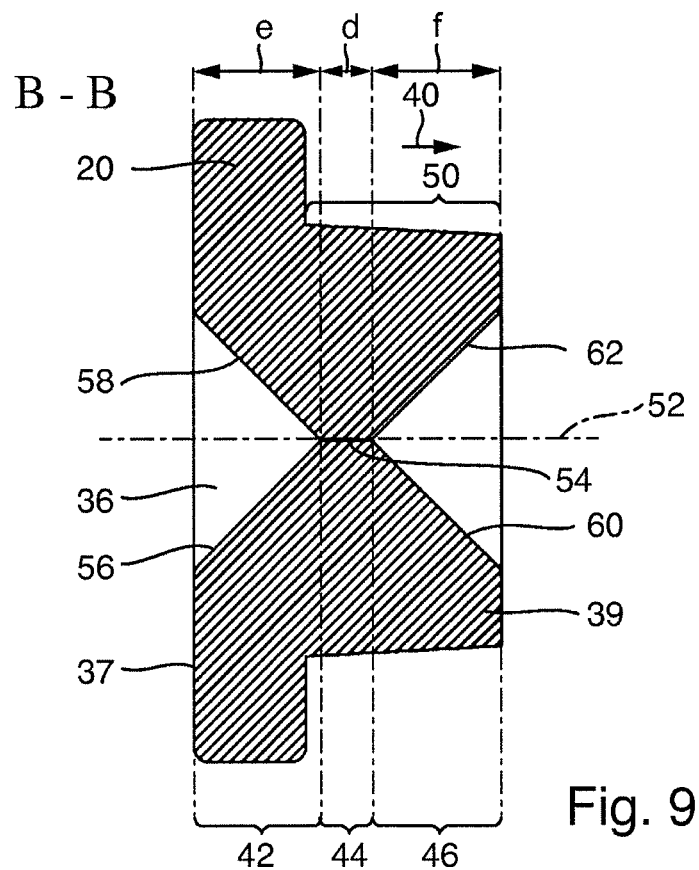
FIG. 9 shows a cross section along line B-B according to FIG. 6.
Figure 10:
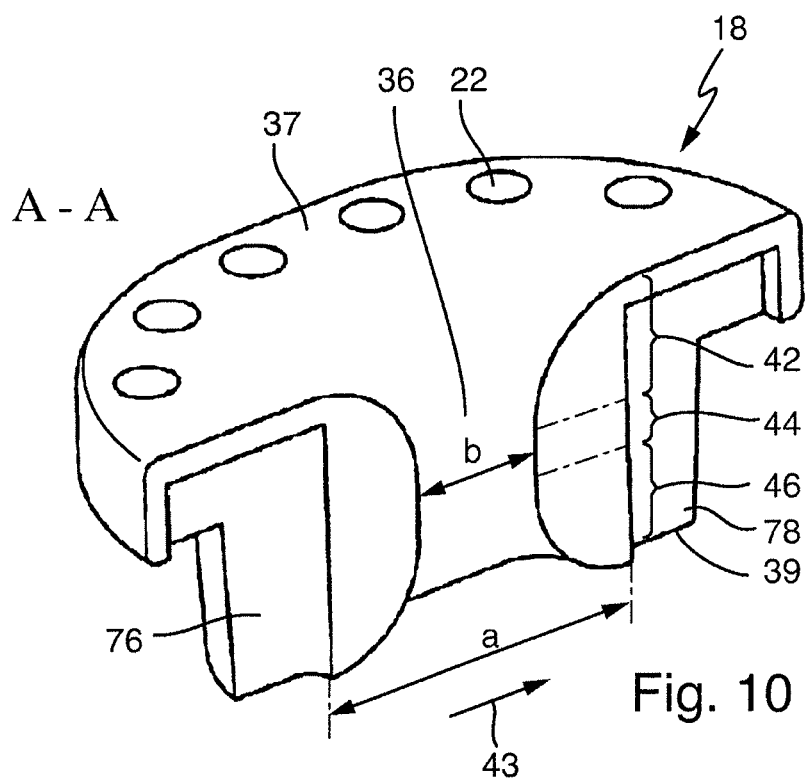
FIG. 10 shows a longitudinal section along line A-A according to FIG. 6 according to a second embodiment.
Figure 12:
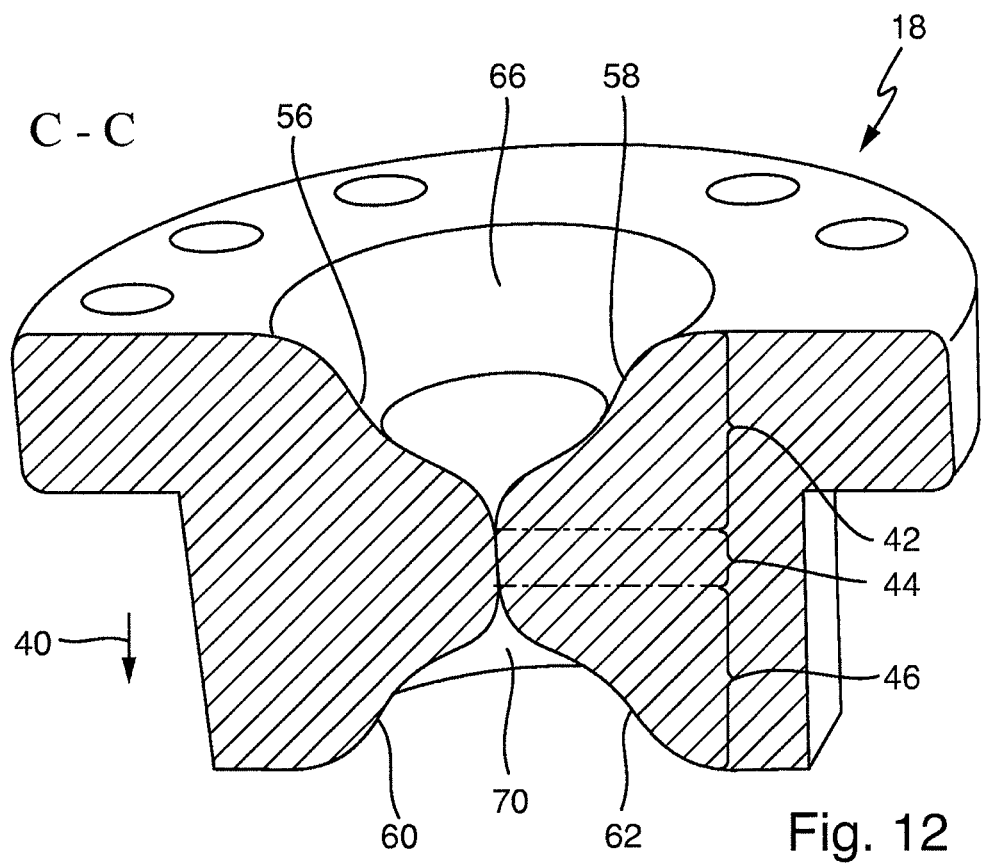
FIG. 12 shows a longitudinal section along line C-C according to FIG. 6 according to a third embodiment.

Taper 42 and extension 46 each have two first sections 56, 58, 60, 62, which are mirror-symmetrical to mirror plane 52, and which have the same transverse extent as slit-shaped valve opening 54 (cf., in particular, FIGS. 10, 12). As can be concluded from FIGS. 9, 10 and 12, respectively two second sections 64, 66, 68, 70 directly adjoin first sections 56, 58, 60, 62, which are formed semi-conically and extend toward corners 72, 74 (cf. FIG. 6) of slit-shaped valve opening section 54.

Figure 7:
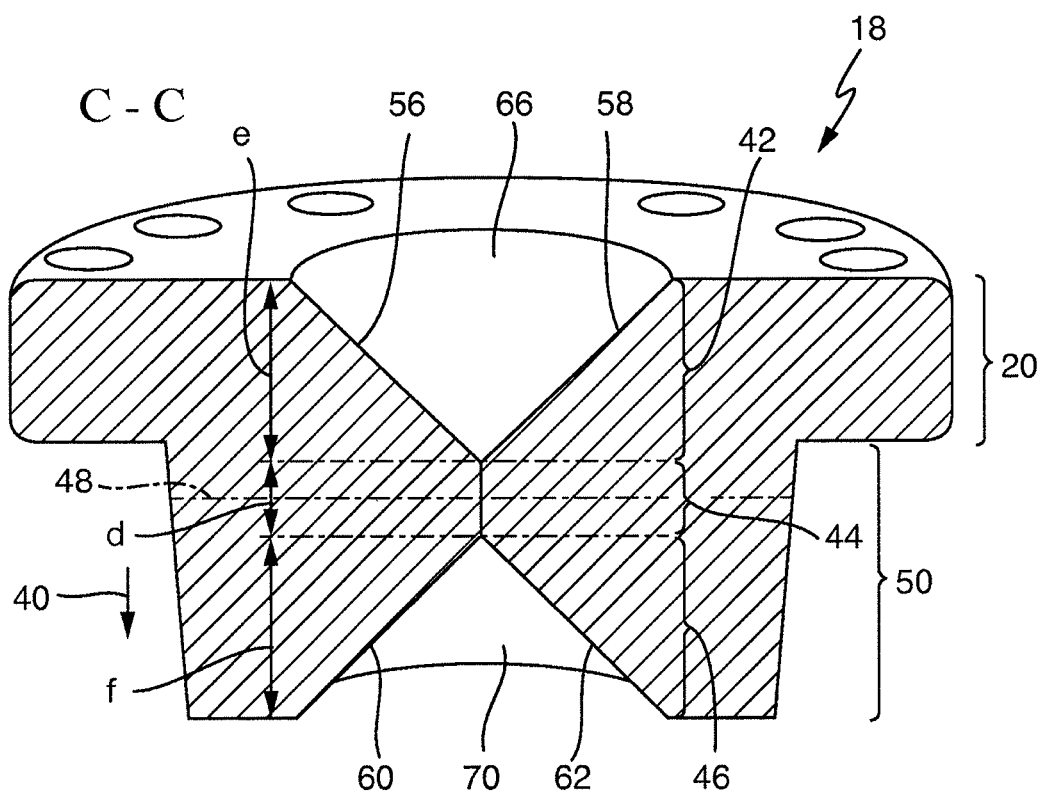
FIG. 7 shows a perspective view of a longitudinal section along line C-C of the valve body according to FIG. 6.
Figure 8:
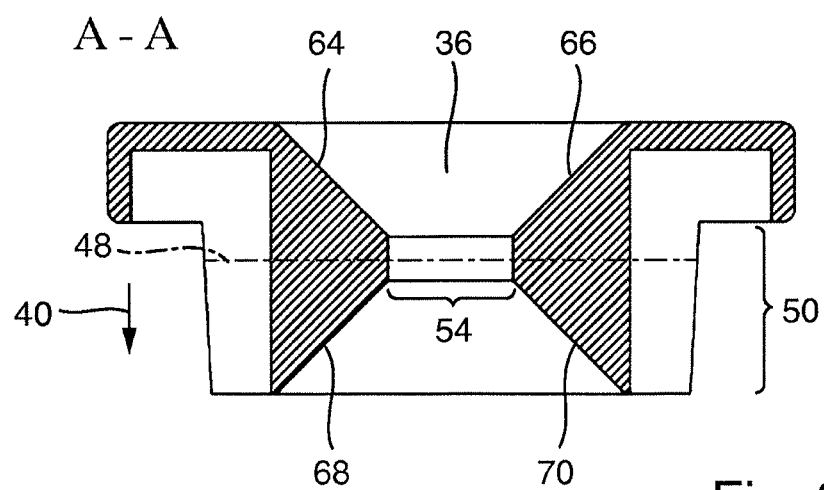
FIG. 8 shows a longitudinal section along line A-A according to FIG. 6.
Figure 11:
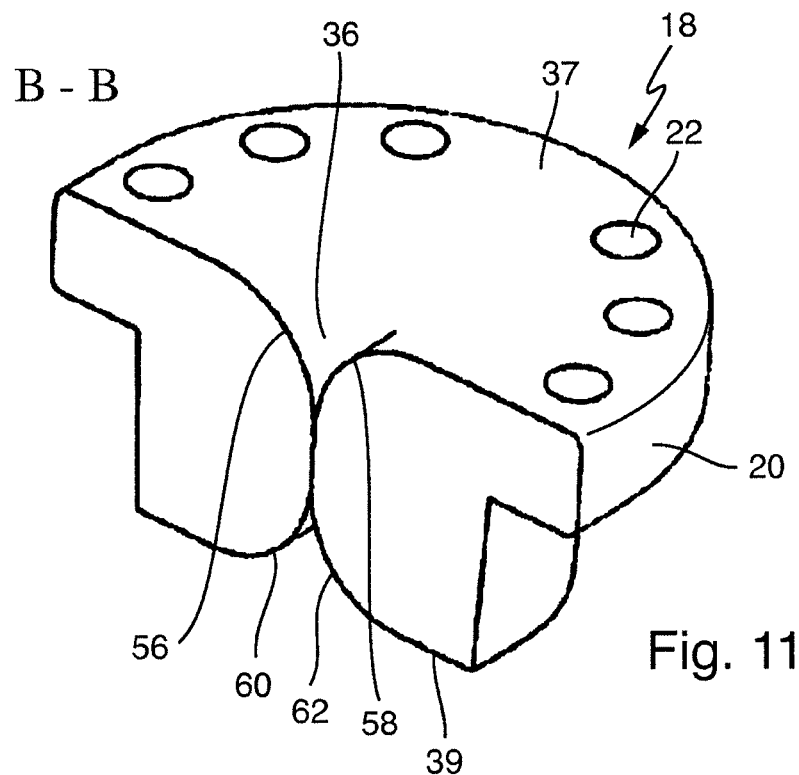
FIG. 11 shows a cross section along line B-B according to FIG. 6 according to a second embodiment.

First sections 56, 58, 60, 62 taper or expand in this instance, according to FIGS. 7 through 9 in a linear manner, according to FIGS. 10 and 11 in a concave arcuate manner and according to FIG. 12 in a waved manner having convex and concave sections. In particular, the waved configuration according to FIG. 12 offers certain advantages concerning the friction when introducing a medical device through valve opening 36.

As it is shown in FIGS. 9 and 10, sealing section 44 in insertion direction 40 has a length d, while taper 42 has a length e and extension 46 has a length f. For this purpose, e=f and e/d equals approximately 2. The ratio e/d generally can be between 1 and 10. According to FIG. 7, valve opening 36 tapers in slit direction 43 from a length a to a length b, ratio a/b being approximately 2. The ratio a/b generally can be between 1.1 and 10.

Figure 5:
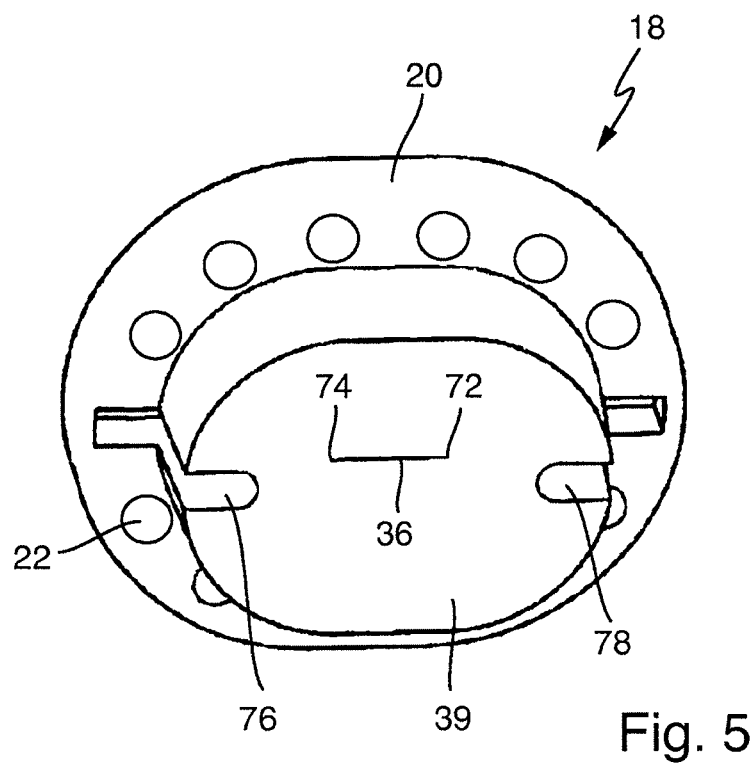
FIG. 5 shows a perspective view of the valve body of the delivery catheter according to FIG. 4.
Figure 6:
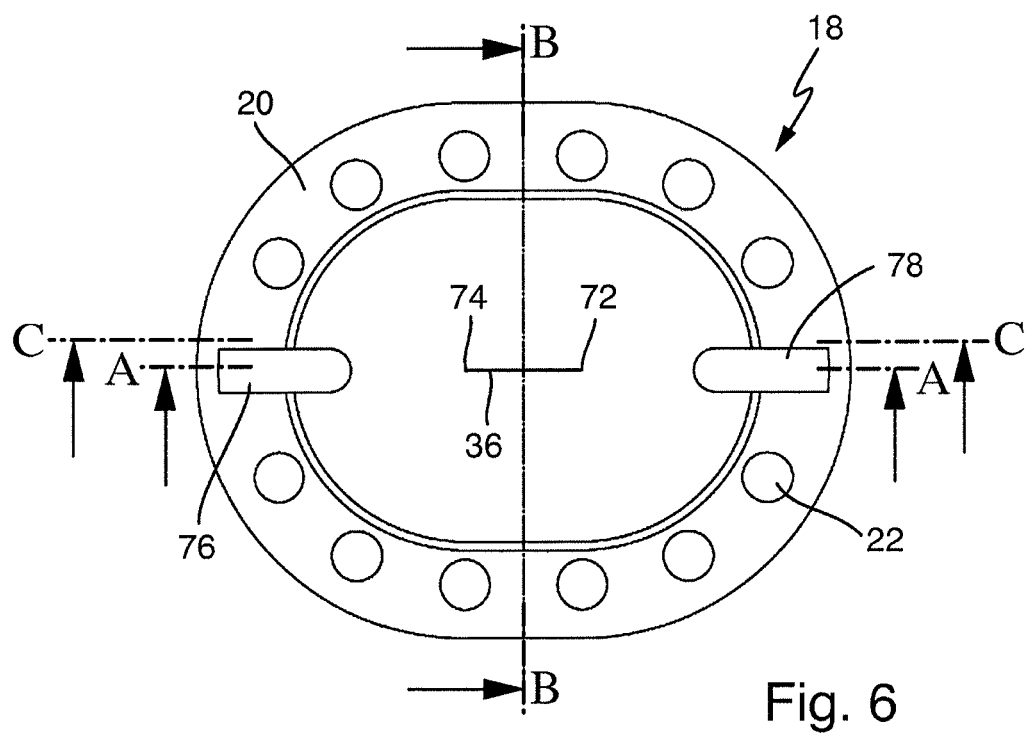
FIG. 6 shows a bottom view of the valve body according to FIG. 5.

As it is in particular shown in FIG. 5, two valve grooves 76, 78 for forming a predetermined breaking point are provided on the outside of valve body 18. In the same plane as these valve grooves 76, 78, delivery catheter grooves 80, 82 are provided, which also represent such a predetermined breaking point (cf. FIG. 4). For this purpose, delivery catheter grooves 80, 82 are introduced during extruding or injection molding of delivery catheter 4 and do not have to be introduced by way of a separate production step.

After a medical device, in particular a catheter, has been introduced through delivery catheter 4 into a blood vessel, catheter 4 can be removed as follows: Head section 10 of catheter 4 has two wings 84, 86. An operator can pull on these wings 84, 86. Then, valve 18 and delivery catheter 4 are broken open in a zipper-like manner and are pulled away from the blood vessel.

For this purpose, valve body 18 is made from silicone having a Shore hardness A between 8-25. Moreover, the valve opening is coated in the region of the sealing section. The coating, in particular, can be made from silicone oil.

If valve body 18 is situated at catheter 4, sealing section 44 is subject to a pretension. This is because elliptical valve body section 50 in the non-disposed state projects beyond receptacle 88 indicated in FIG. 4 along the complete circumference by approximately 0.2 mm. In the disposed state, the elliptical valve body section is consequently compressed so that a pressure force and, for this reason, a pretension act upon sealing section 44. To facilitate the situating of valve body section 18 at attachment section 50, the valve body section tapers slightly in insertion direction 40, as can be seen from FIG. 8. When disposing valve body 18 at attachment section 14, valve body section 50 is consequently subjected to a pressure force, which results in that sealing section 44 assumes a closed position so that valve body 18 is closed in a fluid-tight manner. If a medical device is, for example a catheter having a releasable stent disposed thereon, introduced into a blood vessel in insertion direction 40 through valve opening 36, sealing section 44 is indeed pressed and, for this reason, actuated into the open position. Owing to the pretension acting upon sealing section 44, the medical device is however enclosed in a fluid-tight manner. This is regardless of whether the medical device has a round, oval or similar cross section, and regardless of the size of the cross section. In this instance, pressure forces act in particular perpendicular to the extent of slit-shaped valve opening section 54 in the region of sealing section 44.

To produce delivery catheter-dilator assembly 2, first valve body 18 is disposed at attachment section 14 of delivery catheter 4. Then, holding parts 28, 30 are disposed at delivery catheter 4. Finally, tube section 10 of the dilator is guided through tube section 8 of the catheter and dilator 6 is attached at delivery catheter 4.

Situating this delivery catheter-dilator assembly 2 in a blood vessel can be carried out by way of the Seldinger method. For this purpose, first a vein or artery is opened by a needle and then a guide wire is introduced through the lumen of the needle into the vein or artery. The needle is then withdrawn and delivery catheter-dilator assembly 2 is introduced along the guide wire into the blood vessel. Then, dilator 6 is removed from delivery catheter 4. Subsequently, a medical device, for example a catheter, is introduced in a fluid-tight manner through valve body 18 of delivery catheter 4 into the blood vessel. Thereafter, delivery catheter 4 is pulled apart in a zipper-like manner by pulling on wings 84, 86 and, in so doing, is removed.

What is claimed is:

1. A delivery catheter comprising a valve body having a closeable valve opening for introducing a medical device in insertion direction into, in particular, a blood vessel, characterized in that the valve body is formed in one piece, and that the valve opening, when a medical device is not introduced, tapers in the insertion direction, the valve opening has an extension directly adjoining the sealing section in the insertion direction and expanding when a medical device is not introduced, and a sealing section, which in a closed position at least in sections is subject to a pretension, directly adjoins the taper, so that the sealing section when a medical device is introduced is actuated from the closed position into an open position in such manner that the sealing section encloses the medical device in a substantially fluid-tight manner, wherein the valve opening tapers in the insertion direction in an arcuate or wave-shaped or linear manner toward the sealing section and starting from the sealing section expands in the insertion direction in an arcuate or wave-shaped manner, and wherein the taper and the extension are mirror-symmetrical to a mirror plane extending along the insertion direction through the valve opening, and the valve opening is mirror-symmetrical in relation to a mirror plane extending transverse to the insertion direction through the sealing section.

2. The delivery catheter as recited in claim 1, characterized in that the sealing section in insertion direction is located in the center region of the valve opening.

3. The delivery catheter as recited in claim 1, characterized in that the valve opening in the region of the sealing section is formed in a slit-shaped manner.

4. The delivery catheter as recited in claim 3, characterized in that the valve body section surrounding the valve opening is configured in an elliptical manner and that the valve opening in the region of the sealing section extends transverse to the insertion direction along the major axis of the elliptical valve body section.

5. The delivery catheter as recited in claim 3, characterized in that the taper and/or the extension has/have two first sections, which are mirror-symmetrical to the mirror plane extending in the insertion direction through the valve opening, and that the taper has two second sections extending semi-conically toward the corners of the slit-shaped valve opening.

6. The delivery catheter as recited in claim 1, characterized in that the valve body has a flange section for disposing the valve body at the delivery catheter.

7. The delivery catheter as recited in claim 6, characterized in that the valve body is mounted on an attachment section, wherein the flange section for configuring a plug connection has at least one mandrel or one recess, and the delivery catheter has at least one corresponding recess or one mandrel.

8. The delivery catheter as recited in claim 1, characterized in that the valve body is made from silicone having a Shore hardness A of 8-25, or comprises this material, and/or that the valve opening at least in the region of the sealing section is coated, wherein the coating comprises silicone oil.

9. The delivery catheter as recited in claim 8, characterized in that the outside of the valve body has at least one delivery catheter groove located in the same plane as the valve groove to form a predetermined breaking point, wherein the delivery catheter groove together with the delivery catheter is produced by way of extrusion or injection molding.

10. The delivery catheter as recited in claim 1, characterized in that the outside of the valve body has at least one valve groove for forming a predetermined breaking point.

11. A valve body for a delivery catheter comprising a valve body having a closeable valve opening for introducing a medical device in insertion direction into, in particular, a blood vessel, characterized in that the valve body is formed in one piece, and that the valve opening, when a medical device is not introduced, tapers in the insertion direction, the valve opening has an extension directly adjoining the sealing section in the insertion direction and expanding when a medical device is not introduced, and a sealing section, which in a closed position at least in sections is subject to a pretension, directly adjoins the taper, so that the sealing section when a medical device is introduced is actuated from the closed position into an open position in such manner that the sealing section encloses the medical device in a substantially fluid-tight manner, wherein the valve opening tapers in the insertion direction in an arcuate or wave-shaped or linear manner toward the sealing section and starting from the sealing section expands in the insertion direction in an arcuate or wave-shaped manner, and wherein the taper and the extension are mirror-symmetrical to a mirror plane extending along the insertion direction through the valve opening, and the valve opening is mirror-symmetrical in relation to a mirror plane extending transverse to the insertion direction through the sealing section.

12. A delivery catheter-dilator assembly, comprising a delivery catheter comprising a valve body having a closeable valve opening for introducing a medical device in insertion direction into, in particular, a blood vessel, characterized in that the valve body is formed in one piece, and that the valve opening, when a medical device is not introduced, tapers in the insertion direction, the valve opening has an extension directly adjoining the sealing section in the insertion direction and expanding when a medical device is not introduced, and a sealing section, which in a closed position at least in sections is subject to a pretension, directly adjoins the taper, so that the sealing section when a medical device is introduced is actuated from the closed position into an open position in such manner that the sealing section encloses the medical device in a substantially fluid-tight manner, wherein the valve opening tapers in the insertion direction in an arcuate or wave-shaped or linear manner toward the sealing section and starting from the sealing section expands in the insertion direction in an arcuate or wave-shaped manner, and wherein the taper and the extension are mirror-symmetrical to a mirror plane extending along the insertion direction through the valve opening, and the valve opening is mirror-symmetrical in relation to a mirror plane extending transverse to the insertion direction through the sealing section, and a dilator disposed at the delivery catheter, wherein the dilator in sections extends through the delivery catheter.

\* \* \* \* \*